United States Patent
Pangarkar et al.

(10) Patent No.: US 12,251,292 B2
(45) Date of Patent: Mar. 18, 2025

(54) MULTI-DEVICE INTEGRATION WITH HEARABLE FOR MANAGING HEARING DISORDERS

(71) Applicant: SAMSUNG ELECTRONICS CO., LTD, Gyeonggi-Do (KR)

(72) Inventors: Amol Jayant Pangarkar, Fremont, CA (US); Matthew Corbin Wiggins, San Jose, CA (US); Swapnil Prabhakar Vinod, Fremont, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 676 days.

(21) Appl. No.: 17/487,920

(22) Filed: Sep. 28, 2021

(65) Prior Publication Data
US 2022/0370249 A1  Nov. 24, 2022

Related U.S. Application Data

(60) Provisional application No. 63/192,518, filed on May 24, 2021.

(51) Int. Cl.
*A61F 11/00* (2022.01)
*A61B 5/00* (2006.01)
(Continued)

(52) U.S. Cl.
CPC ............ *A61F 11/00* (2013.01); *A61B 5/0004* (2013.01); *A61B 5/125* (2013.01); *A61B 5/128* (2013.01);
(Continued)

(58) Field of Classification Search
CPC .............. A61F 11/00; G10K 11/17837; G10K 2210/1081; G06N 20/00; A61B 5/0004; A61B 5/125; A61B 5/128; A61B 5/6817
(Continued)

(56) References Cited

U.S. PATENT DOCUMENTS 9,204,998 B2 * 12/2015 Kilgard .................. G09B 23/28
9,992,590 B2 *  6/2018 Baker .................... H04R 25/50
(Continued)

FOREIGN PATENT DOCUMENTS

CN       116156402 A  *  5/2023
CN       117041847 A  * 11/2023
(Continued)

OTHER PUBLICATIONS

Flynn et al., Hearing Performance Benefits of a Programmable Power Baha® Sound Processor with a Directional Microphone for Patients with a Mixed Hearing Loss, Clinical and Experimental Otorhinolaryngology vol. 5, Suppl 1: S76-S81, Apr. 2012 (Year: 2012).*

(Continued)

*Primary Examiner* — Stephanie E Bloss
*Assistant Examiner* — Kevin C Butler
(74) *Attorney, Agent, or Firm* — CUENOT, FORSYTHE & KIM, LLC

(57) ABSTRACT

Hearing management, using a portable device or integrated portable devices, can include generating during a hearing diagnostics phase an audiogram based on responses of a user to signals conveyed to the user. In response to detecting ambient noises during the hearing diagnostics phase, noise cancellation can be performed to cancel the ambient noises in conjunction with conveying the signals to the user. During a hearing enhancement phase, sounds can be captured with the portable device. The captured sounds can be enhanced in real-time during the hearing enhancement phase by amplifying select frequencies of the captured sounds using signal gain. The frequencies can be selected, and the signal gain determined based on the audiogram. The captured sounds, now enhanced, can be conveyed to the user as frequency-enhanced sounds.

18 Claims, 5 Drawing Sheets

(51) Int. Cl.
  *A61B 5/12* (2006.01)
  *G06N 20/00* (2019.01)
  *G10K 11/178* (2006.01)
(52) U.S. Cl.
  CPC .......... *A61B 5/6817* (2013.01); *G06N 20/00* (2019.01); *G10K 11/17837* (2018.01); *G10K 2210/1081* (2013.01)
(58) Field of Classification Search
  USPC .......................................................... 73/585
  See application file for complete search history.

(56) References Cited

U.S. PATENT DOCUMENTS

| | | | | |
|---|---|---|---|---|
| 10,356,535 | B2* | 7/2019 | Van Hasselt | A61B 5/128 |
| 11,393,486 | B1* | 7/2022 | Woodruff | G10L 21/0232 |
| 11,425,516 | B1* | 8/2022 | Gavish | H04R 25/505 |
| 11,921,355 | B2* | 3/2024 | Howell | G02C 11/06 |
| 11,924,613 | B2* | 3/2024 | Sahgal | G10L 25/18 |
| 2017/0230762 | A1* | 8/2017 | Simonides | H04R 25/558 |
| 2017/0230763 | A1* | 8/2017 | Simonides | H04R 25/70 |
| 2017/0230764 | A1* | 8/2017 | Simonides | H04R 25/70 |
| 2017/0230767 | A1* | 8/2017 | Simonides | H04W 4/02 |
| 2017/0230788 | A1* | 8/2017 | Simonides | H04R 25/505 |
| 2018/0035216 | A1* | 2/2018 | Van Hasselt | A61B 5/121 |
| 2018/0203925 | A1* | 7/2018 | Aran | G06F 16/683 |
| 2018/0271710 | A1* | 9/2018 | Boesen | A61B 5/7203 |
| 2019/0231233 | A1* | 8/2019 | Turner | A61B 5/123 |
| 2019/0261095 | A1* | 8/2019 | Brungart | A61B 5/123 |
| 2019/0364354 | A1* | 11/2019 | Keady | H04R 1/1041 |
| 2020/0120422 | A1* | 4/2020 | Rothschild | H04R 3/04 |
| 2021/0056866 | A1* | 2/2021 | Ryu | G09B 21/003 |
| 2022/0295189 | A1* | 9/2022 | Sahgal | H04R 25/353 |
| 2022/0357599 | A1* | 11/2022 | Howell | G02C 11/10 |
| 2022/0370249 | A1* | 11/2022 | Pangarkar | A61B 5/123 |
| 2022/0417647 | A1* | 12/2022 | Sun | H04R 25/505 |
| 2023/0179933 | A1* | 6/2023 | Gavish | A61B 5/123 381/313 |
| 2023/0179934 | A1* | 6/2023 | Gavish | H04R 25/505 381/313 |
| 2023/0232171 | A1* | 7/2023 | Casper | H04R 25/43 |
| 2023/0300532 | A1* | 9/2023 | Spittle | G06F 3/165 381/1 |
| 2023/0336912 | A1* | 10/2023 | Benattar | H04R 5/0335 |

FOREIGN PATENT DOCUMENTS

| | | | | |
|---|---|---|---|---|
| EP | 3884850 | A1* | 9/2021 | ........... A61B 5/4803 |
| EP | 3890357 | A1* | 10/2021 | ........... A63F 13/215 |

OTHER PUBLICATIONS

Nguyen et al., Electroacoustic Evaluation of Smartphone-Based Hearing Aid Applications, Clinical and Experimental Otorhinolaryngology vol. 15, No. 2: 135-143, May 2022 (Year: 2022).*

Berampu et al., Accuracy and Pitfalls in the Smartphone-Based Audiometry, Iranian Journal of Otorhinolaryngology, vol. 36(2), Serial No. 133, Mar. 2024 (Year: 2024).*

* cited by examiner

400

```
┌─────────────────────────────────────────────────────────────────────┐
│ Generate during a hearing diagnostics phase an audiogram based on   │
│ responses of a user to signals conveyed to the user by a portable   │
│ device                                                              │
│ 402                                                                 │
└─────────────────────────────────────────────────────────────────────┘
                                  │
                                  ▼
┌─────────────────────────────────────────────────────────────────────┐
│ Responsive to detecting ambient noises during the hearing           │
│ diagnostics phase, perform noise cancellation to cancel at least    │
│ some of the ambient noises in coordination with conveying the       │
│ signals to the user                                                 │
│ 404                                                                 │
└─────────────────────────────────────────────────────────────────────┘
                                  │
                                  ▼
┌─────────────────────────────────────────────────────────────────────┐
│ Capture sounds with the portable device during a hearing            │
│ enhancement phase                                                   │
│ 406                                                                 │
└─────────────────────────────────────────────────────────────────────┘
                                  │
                                  ▼
┌─────────────────────────────────────────────────────────────────────┐
│ Enhance at least some of the captured sounds in real-time during    │
│ the hearing enhancement phase by amplifying select frequencies of   │
│ at least some of the captured sounds using signal gain, wherein the │
│ frequencies are selected, and signal gain determined, based on the  │
│ audiogram, and wherein at least some of the captured sounds are     │
│ conveyed to the user as frequency-enhanced sounds                   │
│ 408                                                                 │
└─────────────────────────────────────────────────────────────────────┘
```

FIG. 4

MULTI-DEVICE INTEGRATION WITH HEARABLE FOR MANAGING HEARING DISORDERS

CROSS-REFERENCE TO RELATED APPLICATIONS

This application claims the benefit of U.S. Provisional Patent Application No. 63/192,518 filed on May 24, 2021, which is incorporated herein by reference in its entirety.

TECHNICAL FIELD

This disclosure relates to smart devices, including wearables and hearables, and more particularly, to the use of such devices for diagnosing, treating, and enhancing the hearing of device users.

BACKGROUND

Through the convergence of communication and computing technology, various functions can be performed using a single electronic device. Such so-called "smart" devices include the smartphone, which combines telephony with computing functions in a mobile device. Other smart devices include "wearables," like the smartwatch, which are electronic devices worn on or close to the user's body for performing myriad functions including communicating and exchanging data with other devices directly or via a network (e.g., the Internet). Still other smart devices include "hearables," such as smart earbuds, which are electronic in-ear devices that perform multiple functions ranging from wireless communication to fitness tracking.

SUMMARY

In an example implementation, a method can include generating, during a hearing diagnostics phase, an audiogram based on responses of a user to signals conveyed to the user. In response to detecting ambient noises during the hearing diagnostics phase, the method can include performing noise cancellation that cancels at least some of the ambient noises in conjunction with conveying the signals to the user. During a hearing enhancement phase, the method can include capturing sounds with the portable device. The method can include enhancing at least some of the captured sounds in real-time during the hearing enhancement phase by amplifying select frequencies of at least some of the captured sounds using signal gain, the frequencies selected, and the signal gain determined based on the audiogram. The method can include conveying at least some of the captured sounds to the user as frequency-enhanced sounds.

In another example implementation, a system includes a processor configured to initiate operations. The operations may include generating, during a hearing diagnostics phase, an audiogram based on responses of a user to signals conveyed to the user. In response to detecting ambient noises during the hearing diagnostics phase, the operations can include performing noise cancellation that cancels at least some of the ambient noises in conjunction with conveying the signals to the user. During a hearing enhancement phase, the operations can include capturing sounds with the portable device. The operations can include enhancing at least some of the captured sounds in real-time during the hearing enhancement phase by amplifying select frequencies of at least some of the captured sounds using signal gain, the frequencies selected, and the signal gain determined based on the audiogram. The operations can include conveying at least some of the captured sounds to the user as frequency-enhanced sounds.

In another example implementation, a computer program product includes one or more computer readable storage media, and program instructions collectively stored on the one or more computer readable storage media. The program instructions are executable by computer hardware to initiate operations. The operations may include generating, during a hearing diagnostics phase, an audiogram based on responses of a user to signals conveyed to the user. In response to detecting ambient noises during the hearing diagnostics phase, the operations can include performing noise cancellation that cancels at least some of the ambient noises in conjunction with conveying the signals to the user. During a hearing enhancement phase, the operations can include capturing sounds with the portable device. The operations can include enhancing at least some of the captured sounds in real-time during the hearing enhancement phase by amplifying select frequencies of at least some of the captured sounds using signal gain, the frequencies selected, and the signal gain determined based on the audiogram. The operations can include conveying the captured sounds to the user as frequency-enhanced sounds.

This Summary section is provided merely to introduce certain concepts and not to identify any key or essential features of the claimed subject matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

FIG. 4 illustrates an example method of managing a user's hearing using a system to coordinate multiple integrated devices.

DETAILED DESCRIPTION

Figure 1:
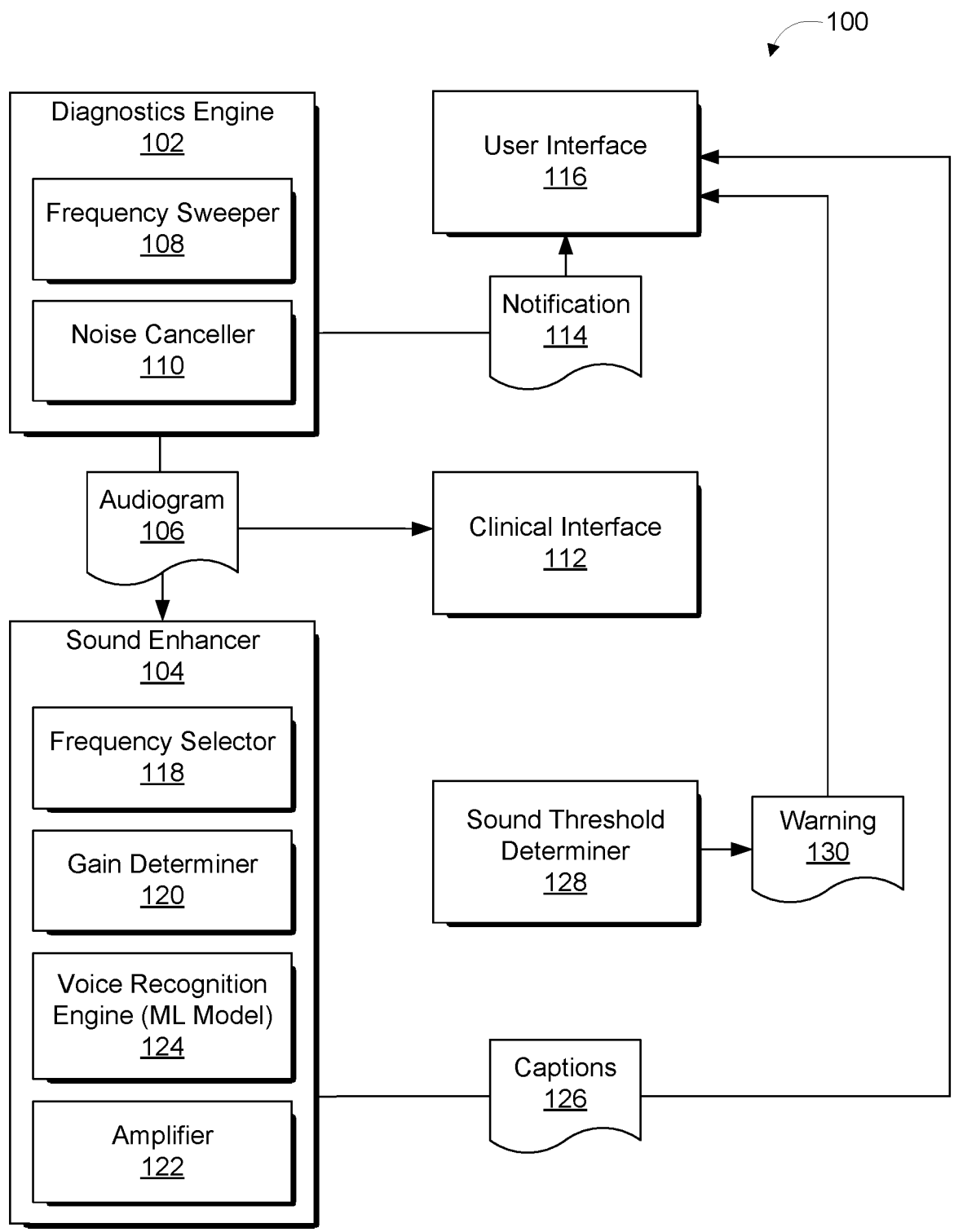
FIG. 1 illustrates an example hearing management system.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to smart devices, including wearables and hearables, and more particularly, to the use of such devices to diagnose, treat, and enhance the hearing of device users. There are electronic systems, both as standalone devices like hearing aids and ones integrated in other devices, that perform different functions to help manage a user's hearing. Conventional devices do not provide multi-modal data acquisition using separate, but operatively coupled devices, which also perform different functions for monitoring, diagnosing, and treating various hearing conditions of a user.

In accordance with the inventive arrangements described within this disclosure, example methods, systems, and computer program products are provided that are capable of performing diverse hearing functions using multi-modal data acquisition and processing by multiple devices integrated into a single system. The example implementations described herein may be implemented in a single device that is operatively coupled with and controls one or more other devices. The cooperatively functioning devices can comprise a combination of mobile device (e.g., smartphone), wearable (e.g., smartwatch), hearable (e.g., earbuds), or other smart device that combines communication and computing capabilities.

In one or more example implementations, a system implemented in hardware and/or software of one device can control multiple devices. Functioning cooperatively under the control of the system, the devices can monitor, test, and treat different hearing conditions of a user of the devices. One function the system-controlled devices are capable of performing is the testing of the user's hearing. In accordance with the inventive arrangements disclosed herein, the devices can generate an audiogram that without the immediate presence of a clinician or specific medical device is equivalent, or approximately so, to a clinical grade audiogram. The audiogram is generated in response to testing the user's hearing acuity at different frequencies. Based on the user's responses to test signals (e.g., tones), the audiogram indicates the degree to which the user hears sounds at the different frequencies (e.g., high-pitched versus low-pitched sounds measured in Hertz (Hz)) in terms of the sound's intensity or loudness (measured in decibels (dB)). The audiogram can provide separate results for the user's left ear and right ear.

The devices in one aspect detect and cancel ambient noises that would otherwise corrupt the results of the audiogram. The audiogram can be created based on a sweep of signal frequencies conveyed to the user at different amplitudes through one device and to which the user responds using another device. One device can generate a recommendation to the user based on the results. For example, a device can compare the user's assessed sensitivity to sounds at different frequencies with a predetermined set of thresholds. Based on the comparison, the same or another device can recommend, for example, that the user consult a hearing specialist (e.g., physician or audiologist). One device can establish a communication link for conveying the audiogram to the hearing professional over a communication network.

Based on the audiogram one system-controlled device can manage gain settings in reproducing sounds to conveyed to the user from the same or another device so as to enhance the user's hearing. In certain arrangements, using a wearable or mobile device cooperatively operating in conjunction with a hearable, the system-controlled devices in real-time during a conversation can tune the conveyance of signals generated in response to a device-detected conversation, the tuning operating to amplify certain frequencies. The selection of frequencies to tune, as well as the gain setting by which the selected frequencies are amplified, can be based on the results of an audiogram produced by the system-controlled devices during an earlier hearing diagnostics phase. In addition to conveying sounds of the conversation via a hearable, a mobile device, as needed, can perform real-time captioning of the conversation, the captions displayed on a visual screen of the mobile device operating in conjunction with the hearable.

Taking into account the fact that a user is often unknowingly exposed to sounds whose loudness can adversely affect the user's hearing, the system-controlled devices also can monitor ambient sounds and warn the user of potentially harmful sounds that exceed a predetermined threshold.

In one or more example implementations, the system-controlled devices are capable of managing a user's tinnitus. Based on the audiogram produced by the devices, the user's tinnitus can be managed and treated using a hearable that compensates for or amplifies sounds based on the audiogram generated by the devices during a hearing test phase. A mobile device can, in accordance with a user's selection, implement notch therapy to treat the tinnitus or noise masking to relieve the symptoms. The mobile device can convey via the hearable sounds (e.g., white noise, music) with one or more audiogram-determined tinnitus frequencies eliminated so as to subconsciously train the user to ignore tinnitus frequencies. One or more system-controlled devices also are capable of implementing notch therapy with real-time audio, as well. A wearable, in still other arrangements, can detect when the user is sleeping and provide soothing white noise to help the user sleep despite the user's tinnitus. The system is capable of providing a user the option of two separate treatments for the user's tinnitus: notch therapy to remove one or more tinnitus frequencies, and generic white noise therapy to distract the user.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

Figure 5:
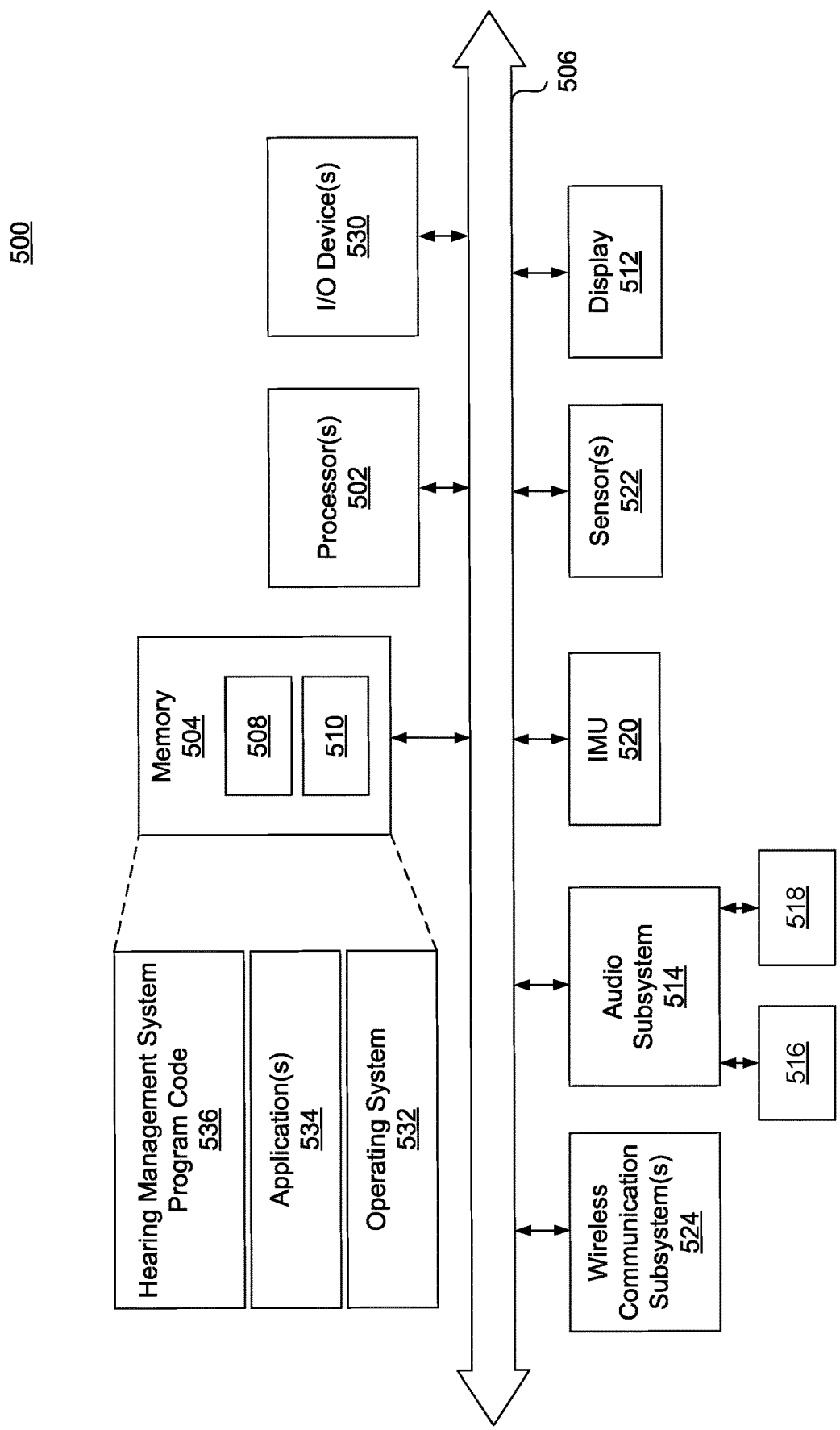
FIG. 5 illustrates an example device for implementing a hearing management system.

FIG. 1 illustrates an example hearing enhancement system (system) 100. System 100 can be implemented within a device such as mobile device, wearable device, or hearable device. Elements of the device can include those described herein in connection with device 500 (FIG. 5). System 100 can be implemented in hardware (e.g., dedicated, hardwired circuitry), software (e.g., program code executed by one or more processors), or a combination of hardware and software. System 100, in certain embodiments is implemented in a first device and is capable of controlling one or more other devices communicatively linked with the first device. In other embodiments, system 100 comprises elements dispersed among multiple devices. In every arrangement, system 100 is capable of integrating multiple, portable devices (e.g., mobile devices, wearables, hearables), which through integration and control by system 100, are capable of performing the various testing, analyzing, enhancing, monitoring, and other hearing-related operations described herein. System 100 illustratively includes diagnostics engine 102 operatively coupled with sound enhancer 104.

Diagnostics engine 102 is capable of generating audiogram 106 based on signals conveyed by a portable device to a user. In certain embodiments, the signals can be generated by a first device (e.g., mobile device) and conveyed to a user through a second device (e.g., hearable) operatively coupled with and controlled by the first device during a hearing diagnostics phase. Diagnostics engine 102, in some arrangements, includes frequency sweeper 108 operatively coupled with noise canceller 110. Frequency sweeper 108 can sweep through a predetermined frequency spectrum (e.g., 20 Hz to 20 kHz) to test the user's ability to hear sounds (e.g., pure tones, audible words) at different frequencies with various intensities.

During the hearing diagnostics phase, noise canceller 110 detects ambient noises. Ambient noises, in certain embodiments, can be detected with a microphone of a first device (e.g., mobile device), another of a second device (e.g., hearable), another of a third device (e.g., wearable), or any combination thereof to enhance system 100's sound detection capabilities by using multiple, dispersed devices. As test sounds at varying frequencies and intensities are presented to the user with a device (e.g., a pair of earbuds), noise canceller 110 responds to the detecting of ambient noise by generating antiphase sounds (sounds of equal amplitude and frequency but inverse phase with respect to the ambient noise) to cancel some or all of the ambient noise. Noise canceller 110 can cancel some or all of the ambient noise in conjunction with conveying signals (sounds at varying frequencies and intensities) to the user during the hearing diagnostics phase. For example, in certain arrangements, noise canceller 110 performs noise cancellation in real-time in conjunction with the conveying so as to cancel all or some ambient noise as the signals are conveyed to the user. The signals may be conveyed to the user via a hearable, for example, and as ambient noises are detected by a microphone of the hearable or a mobile device or wearable, noise canceller 110 simultaneously cancels all or some of the ambient noise. In some embodiments, noise canceller 110 also cancels some or all ambient noise as the user responds to the signals conveyed.

Audiogram 106 is generated by diagnostics engine 102 based on the user's responses to the sounds presented to the user at different frequencies. Noise cancellation performed by noise canceller 110 enhances the accuracy of audiogram 106. Noise canceller 110 mitigates or eliminates entirely ambient noises that could otherwise corrupt the results of audiogram 106. Audiogram 106 generated by diagnostic engine 102 thus more closely approximates, if not duplicates, a clinical-grade audiogram that would be produced in a largely noise-free clinical setting.

Optionally, system 100 can convey, either automatically or in response to user input, audiogram 106 via clinical interface 112. Clinical interface 112 can include a wireless connection to a network (e.g., cellular) linking a device controlled by system 100 to a clinician (e.g., physician or audiologist). Additionally, system 100 can generate notification 114 (e.g., a text or voice message), which can be conveyed to the user via one of the devices controlled by system 100 notifying the user of the results of audiogram 106 and advising the user to pursue an indicated action (e.g., consult a hearing specialist). The notification specifying the results of audiogram 106 can assist a clinician in pursuing further testing and/or treatment of a suspected hearing condition of the user.

Sound enhancer 104 is capable of enhancing the user's hearing based on audiogram 106. Operating during a hearing enhancement phase, the system 100 can direct a portable device or multiple integrated devices to enhance a user's hearing by amplifying some or all portable device-captured sounds using signal gain applied to select frequencies. The frequencies are selected, and the signal gain determined by sound enhancer 104 based on the audiogram 106 generated during the hearing diagnostics phase. In certain embodiments, sounds (e.g., conversations, music) are captured by a microphone embedded in or operatively coupled with a first device (e.g., mobile device), a second device (e.g., hearable), and/or a third device (e.g., wearable). Sound enhancer 104 can amplify sounds at frequencies selected based on audiogram 106, the amplification according to a gain also determined from audiogram 106.

Illustratively, sound enhancer 104 includes frequency selector 118, gain determiner 120, and amplifier 122. Frequency selector 118 selects frequencies that audiogram 106 indicates are ones the user is not capable of hearing at a minimum threshold deemed normal for a human. For selected frequencies, gain determiner 120 based on the degree of hearing impairment indicated by audiogram 106 determines a signal gain. The signal gain needed for enhancing the user's hearing can be determined based on a differential between the intensity or loudness of a sound necessary for the user to hear the sound (indicated by audiogram 106) and a normal loudness. The normal loudness can be determined based on a statistical sampling of a population of individuals (e.g., cohorts within the same age range) having healthy hearing. The signal gain provided can also be personalized by providing gain settings to the user, who can perform a repeat testing to generate another audiogram in order to ensure that the gain settings work well for enhancing the user's hearing.

Amplifier 122 amplifies sound by applying frequency-specific signal gain determined by gain determiner 120 to sounds captured by microphones of one or more devices under system 100's direction. Amplifier 122 can be configured to perform digital signal processing (DSP). Using DSP, amplifier 122 can reproduce sounds captured by the microphones but enhanced through signal gain or amplification with respect to the frequencies selected by frequency selector 118 based on audiogram 106. Sound enhancer 104 is capable of amplifying select frequencies of sound based on the audiogram in real-time during an enhancement phase and in response to detection of sounds captured by the microphones of one or more devices and conveyed to the user through one of the devices (e.g., hearable) under direction and control of system 100.

Optionally, system 100 can also include voice recognition engine 124. Voice recognition engine 124 can process a conversation in parallel with or prior to the operations of amplifier 122. Voice recognition engine 124 can generate conversation captions 126 by converting to text the speech that is detected by microphone(s) embedded in one or more devices controlled by system 100. Conversation captions 126 can further enhance a user's comprehension of conversations in real-time.

In certain embodiments, voice recognition engine 124 implements a machine learning model that learns to recognize words or phrases or their repetition as indicating a user's difficulty in comprehending words spoken during a conversation. For example, a deep learning neural network trained through supervised learning can be implemented by voice recognition engine 124. The deep learning neural network can learn that certain phrases such as "what was that you said" or repetition of a phrase such as "would you repeat that" indicate that the user is experiencing difficulty understanding a conversation. Based on classifying the words or phrases, voice recognition engine 124 can respond by initiating real-time generation of captions during the conversation.

In still other embodiments, system 100 optionally can include sound threshold determiner 128. Sound threshold determiner 128 can monitor sounds captured by microphones of one or more devices controlled by system 100 to detect sounds at decibel levels that are potentially injurious to the user's hearing. Because there are times in which the loudness of sounds increases almost imperceptibly or are not immediately recognized as being harmfully loud, sound threshold determiner detects sounds that are above a predetermined threshold loudness and generates warning 130 in response. Warning 130 can be conveyed to the user visually or audibly via user interface 116.

System 100, in yet other embodiments, is capable of detecting, monitoring, treating, and/or relieving hearing conditions of the user such as tinnitus. Audiogram 106 can be generated by diagnostic engine 102 following identification of one or more tinnitus frequencies afflicting the user. The user can initiate a tinnitus mode in which system 100 directs a device (e.g., a hearable) to manage the user's tinnitus. In certain arrangements, system 100 allows the user to select different tinnitus treatments, including notch therapy and white noise generation. Notch therapy can be provided by system 100 with respect to one or more tinnitus frequencies identified by the user based on the system-generated audiogram and can be marked by the user during the system-performed frequency sweep. System 100, in response to a user's alternative selection, generates white noise to train the user subconsciously to ignore identified tinnitus frequencies.

In one embodiment, system 100 is configured to detect when the user is sleeping and provide soothing white noise to help the user sleep better. For example, system 100 can use an inertial measurement unit (IMU) of a device (e.g., earbuds, smartwatch) to detect the absence of movements for a predetermined duration, indicating that the user is resting. In response, system 100 can initiate the generation of white noise, generation of which continues until detection of movement suggesting that the user is awake and active.

Figure 2:
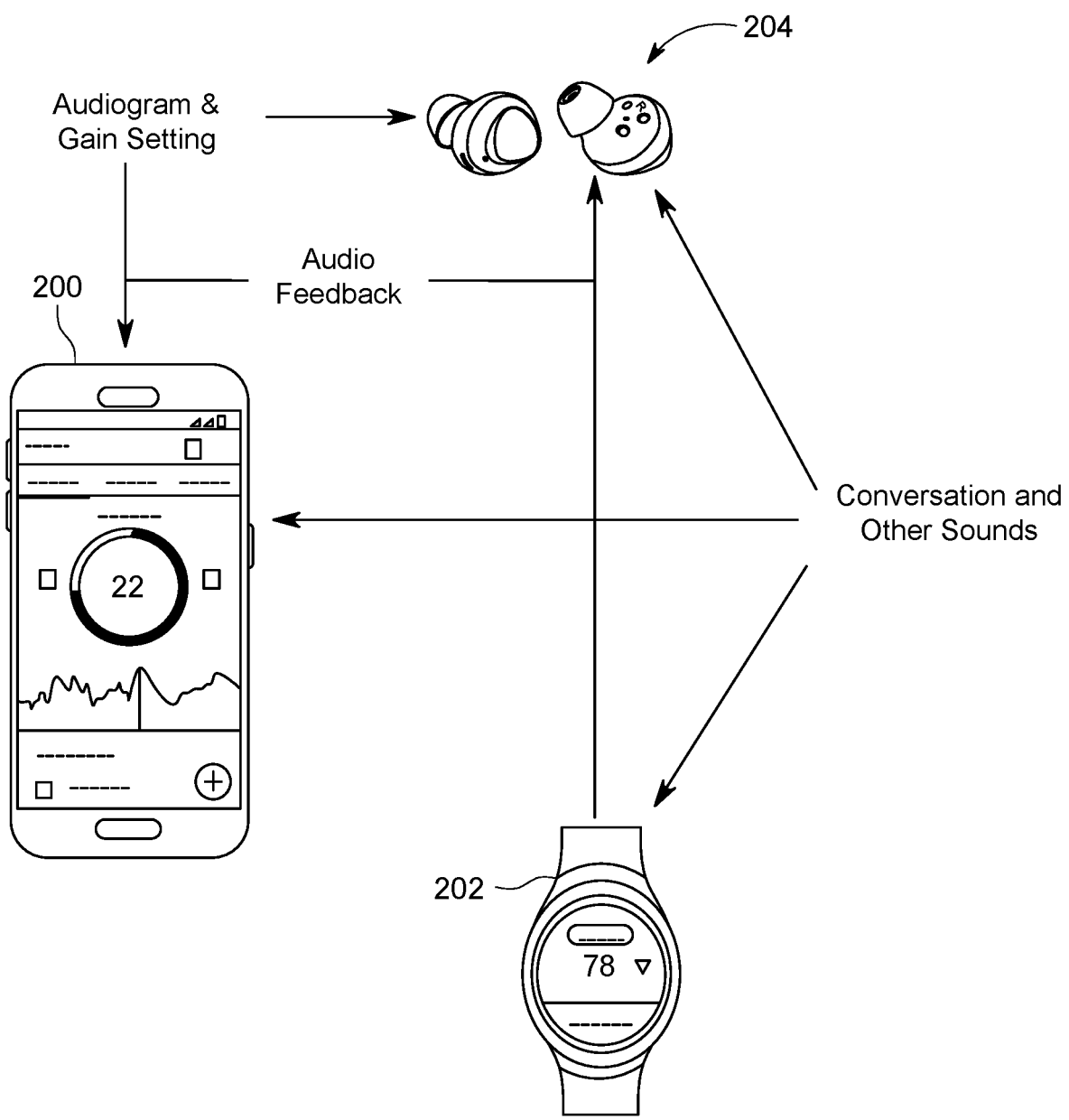
FIG. 2 illustrates an example assemblage of integrated devices that cooperatively operate under the direction of the system of FIG. 1.

Referring additionally to FIG. 2, an example arrangement of devices controlled by system 100 is illustrated. Smartphone 200 is an example mobile device. Earbuds 202 are an example hearable, and smartwatch 204 is an example wearable. Smartphone 200, earbuds 202, and smartwatch 204 operate cooperatively under the direction and coordination of system 100. Smartphone 200 can be positioned within an arm's reach of the user. Smartphone 200 can comprise an onboard speaker and onboard microphone. Smartphone 200 can provide interface capabilities (e.g., display) and wireless communication capabilities (e.g., cellular, Wi-Fi, Bluetooth). Smartphone 200 also can include audio signal processing capabilities.

Earbuds 202 can include an inner-ear facing speaker and an outward facing microphone directed approximately 180 degrees from, or opposite to, the direction inner-ear speaker faces so as to detect sounds heard by the user. Likewise, earbuds 202 also can be endowed with onboard audio signal processing capabilities, as well as wireless communication capabilities (e.g., cellular, Wi-Fi, Bluetooth). In certain embodiments, earbuds 202 are also configured in hardware or software or a combination thereof to generate on separate channels both noise cancellation signals and white noise. Smartwatch 204 likewise includes an onboard speaker and onboard microphone, as well as interface capabilities, audio signal processing capabilities, and wireless communication capabilities (e.g., cellular, Wi-Fi, and Bluetooth).

Diagnostic engine 102 of system 100 can be implemented, for example, in smartphone 200. In a diagnostic phase during which diagnostic engine 102 generates audiogram 106, one or more of the microphones of smartphone 200, earbuds, 202, and/or smartwatch 204 can capture ambient sounds. Signal processing by noise canceller 110, implemented in smartphone 200, earbuds 202, or smartwatch 204, mitigates or eliminates entirely the noise, providing a quiet ambient environment for the user during which testing tones of varying frequency (both separately and jointly), duration, and intensity are generated by frequency sweeper 108, implemented for example by smartphone 200, and are presented to the user through the speakers of earbuds 202 and/or smartphone 200. The user interface of smartphone 200 enable the user to respond to the audible stimuli. Optionally, smartphone 200 can record the user's responses.

Smartphone 200, using one or more of the onboard microphones (its own and/or those of the earbuds 202 and/or smartwatch 204) can continue actively monitoring background sounds during the hearing diagnostics phase. Noise canceller 110 continues to provide noise cancellation in response to detecting ambient noise while diagnostic engine 102 simultaneously generates audiogram 106 in response to the user's listening to the audio stimuli and responding. User interface 116 can be implemented by the smartphone 200 or smartwatch 204 to enable sharing of audiogram 106 with a physician, audiologist or other hearing specialist. The microphone of smartphone 200, in some embodiments, can be used to record ambient noise, which system 100 can analyze the frequency of to inform the user about potential contamination of audiogram 106 at those specific frequencies.

Notification 114, based on the analysis, can recommend the user retake the audiogram in the future or take an alternative or additional action, such as contacting a hearing specialist. For example, notification 114 can recommend the user retest using the system in response to a likelihood that audiogram 106 is corrupted by ambient noise, the likelihood arising because ambient noise exceeds a predetermined threshold. Based the user's hearing acuity measured by audiogram 106, as compared with a set of predetermined set of minimal hearing thresholds, notification 114 can recommend that the user consult the hearing specialist (e.g., physician or audiologist), for example.

In certain embodiments, earbuds 202 (or other hearable) can implement sound enhancer 104. Based on audiogram 106 and audio feedback from earbuds 202, smartphone 200 can implement frequency selector 118 to select frequencies that are amplified by amplifier 122 in accordance with the gain determined by gain determiner 120 to compensate for any hearing deficiencies of the user and thereby enhance the user's overall hearing of sounds (e.g., conversations). Smartphone 200 or smartwatch 204 optionally can implement voice recognition engine 124 to generate captions 126 in real-time to supplement visually with text the enhanced sounds conveyed through speakers of smartphone 200, earbuds 202, or smartwatch 204. The arrangement described is only one example of implementation of system 100. System 100 can be implemented entirely in one device or, in other embodiments, distributed among multiple, integrated devices cooperatively controlled by system 100.

Figure 3:
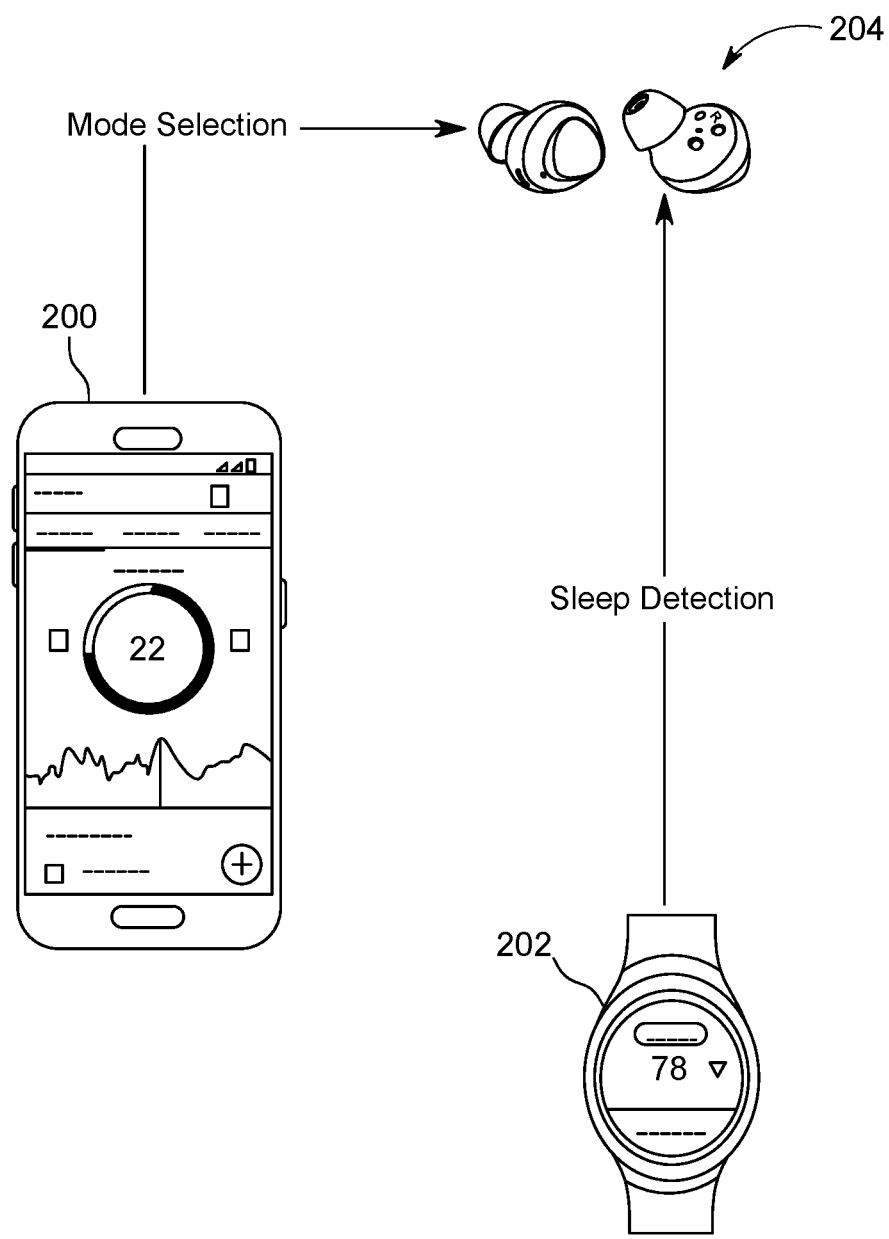
FIG. 3 illustrates an example assemblage of integrated devices that cooperatively operate under the direction of the system of FIG. 1 for treating a user's tinnitus.

Referring additionally to FIG. 3, an example arrangement of devices controlled by system 100 is illustrated whereby the devices are configured to treat a user's tinnitus. Illustratively, smartphone 200 provides an interface with which the user selects different modes. In one mode, earbuds 202 implement sound enhancer 104. Frequency selector 118 identifies one or more tinnitus frequencies specific to the user, and gain determiner 120 can determine a gain with which amplifier 122 amplifies sounds at certain frequencies. Earbuds 202 can eliminate a tinnitus frequency and amplify other sounds such that the user's perception of other frequencies is enhanced while learning to ignore the tinnitus frequency. In another mode, earbuds 202 can generate a full spectrum of sounds, minus one or more tones at the frequencies of the user's tinnitus, so that by listening to sounds (e.g., music, white noise, amplified external sounds) without hearing the specific tinnitus frequencies the user may learn to subconsciously ignore tinnitus frequencies.

With respect to treating the user's tinnitus, the system-generated audiogram can reveal two pertinent conditions. First, whether the user has hearing loss at certain frequencies, and second, whether the user is afflicted by tinnitus at one or more other frequencies. The system increases the gain settings to enhance the amplitude at hearing loss frequencies but does not enhance the other frequencies (gain=1) and removes the tinnitus frequency (gain=0). Through repeated listening to sounds in this manner, the user subconsciously learns to tune out any tinnitus frequencies.

Earbuds 202, additionally or alternatively, can generate soothing white noise to help the user sleep better. Optionally, system 100 can detect when the user is sleeping before initiating generation of the white noise. For example, using an IMU of smartphone 200, earbuds 202, or smartwatch 204, the user can determine the user is resting or sleeping ("rest state") based on a lack of detected movement over a predefined duration. Conversely, system 100 can stop generation of the white noise in response to IMU-detected movement indicating that the user is awake and active. Additionally, or alternatively, the user can use a sleep scheduler of a device (e.g., smartphone, wearable) such that the white noise generation occurs at specific times the user sets.

FIG. 4 illustrates an example method controlling multiple devices for managing a user's hearing. The method can be implemented in a single device or distributed among multiple devices as described in the context of FIGS. 1-3. The devices can include a mobile device, a wearable, and/or a hearable as illustrated by FIGS. 1-3.

At block 402, the system operating in a hearing diagnostics phase, generates an audiogram based on responses of a user to signals conveyed to the user by a portable device. The portable device can implement diagnostics engine 102, which includes frequency sweeper 108 for generating signals (e.g., pure tones) at different frequencies that are presented to the user and to which the user responds for determining the hearing acuity of the user. The portable device, in certain embodiments can comprise two integrated devices that cooperatively function under the control of the system. For example, the generation of the signals can be performed by a smartphone and the signals conveyed to the user via a pair of earbuds. The user's response can be captured by the smartphone.

At block 404, in response to detecting ambient noises during the hearing diagnostics phase, the system performs noise cancellation that cancels some or all the ambient noises when the signals are conveyed to the user. The portable device can implement noise canceller 110, which performs the noise cancellation to create an environment relatively free of extraneous noise for testing the user's hearing. In certain embodiments in which the system controls distinct portable devices, the noise cancellation can be performed by smartphone or, in other embodiments, by the earbuds.

At block 406, during a hearing enhancement phase, the system captures sounds with the portable device. In certain embodiments, to further enhance sound capture, the system can utilize the microphones of a smartphone, earbuds, and optionally, even the microphone of a third device, a smartwatch, with the separate devices integrated under the operative control of the system.

At block 408, the system enhances some or all the captured sounds in real-time during the hearing enhancement phase. The system enhances captured sounds by amplifying select frequencies of some or all the captured sounds using signal gain. The system can implement frequency selector 118 for selecting frequencies to amplify and gain determiner 120 for determining the gain applied at each frequency. The frequencies are selected, and the signal gain determined, based on the audiogram generated during the hearing diagnostics phase. Some or all captured sounds, which are now enhanced by amplification, are conveyed by the system to the user as frequency-enhanced sounds. In certain embodiments in which the system controls multiple integrated devices, the enhancement can be performed by the earbuds, which enhance some or all captured sounds based on the audiogram generated by the smartphone during the hearing diagnostics phase.

The system can generate a hearing assessment by analyzing the audiogram with the portable device. In some embodiments, the portable device can be a smartphone. The smartphone can operate independently under the control of the system or jointly with one or more other portable devices (e.g., earbuds). The system can provide through the portable device a hearing treatment recommendation based on a determination, through the hearing assessment, that the user suffers potential hearing degradation. Hearing degradation can be measured, for example, based on a differential between the user's sensitivity to tones at one or more specific frequencies versus one or more thresholds deemed normal in accordance with a statistical sampling of a population. The hearing treatment recommendation can advise the user to consult a hearing professional (e.g., physician or audiologist). The system can establish with the portable device (e.g., smartphone) a wireless connection with a communication network for conveying the audiogram to a predetermined communication network site. The communication network site can be that of a hearing professional who can provide a further assessment of the user's hearing. The system can also enable the importing over the communication network an audiogram generated under the direction of a hearing professional.

In some embodiments, the system can implement voice recognition to recognize a likely hearing difficulty of the user during a conversation captured by one or more portable devices. In response to detecting a likely hearing difficulty, the system can generate conversation captions. The conversation captions can be displayed with the portable device in response to the detecting the likely hearing difficulty. In certain embodiments, the captions can be presented to the user on a display, such as the screen of a smartphone operating alone or in conjunction with other devices under the control of the system. In some embodiments, the system can perform voice recognition using a machine learning mode that is trained to detect the likely hearing difficulty based on classifying one or more words or phrases detected during the conversation.

The system can detect potentially harmful sounds during a monitoring phase distinct from both the hearing diagnostics and hearing enhancement phases. During the monitoring phase, the system using one or microphones of one or more portable devices (e.g., smartphone, smartwatch, earbuds) can detect potentially harmful sounds. Typically, sounds are potentially harmful if sufficiently loud for a certain period. Accordingly, in response to determining that a sound is sufficiently loud and/or heard over a time interval as to be potentially harmful (e.g., exceeding a predetermined threshold and/or for a predetermined time), the system can generate a warning that is conveyed to the user. For example, a visual warning can be provided on the screen of a smartphone or smartwatch. An audible warning, for example, can be provided by either such device or through a pair of earbuds. The warning can be provided by the system in real-time so that the user can avoid unnecessary exposure to the potentially harmful sounds.

Method 400 can also include controlling one or more integrated devices to manage or treat a user's tinnitus. The system can provide a tinnitus therapy to the user based on the user's selection of one of a plurality of tinnitus therapy options presented to the user via a portable device (e.g., screen of a smartphone). The plurality of therapy options can include notch therapy with respect to one or more identified tinnitus frequencies. In some embodiments, the system can identify one or more tinnitus frequencies by performing tinnitus sound matching using sounds generated by and conveyed to the user. Optionally, the system can use an IMU or similar sensor of a portable device (e.g., earbuds, smartwatch) to determine a rest state of the user. The system can detect the user rest state by sensing the user's lack of movement over a predetermined interval. The system can initiate an audible tinnitus treatment performed by the portable device in response to the detecting the rest state of the user. The sounds also can be generated and conveyed at specific times set in response to user input.

FIG. 5 illustrates an example portable device 500 whose elements, all of which or only select ones, may be incorporated in a portable device (e.g., smartphone, earbuds, smartwatch) used to implement a hearing management system, such as system 100. Device 500 includes one or more processors 502 coupled to memory 504 through interface circuitry 506. Device 500 stores computer readable instructions (also referred to as "program code") within memory 504, which is an example of computer readable storage media. Processor(s) 506 execute the program code accessed from memory 504 via interface circuitry 506.

Memory 504 can include one or more physical memory devices such as local memory 508 and bulk storage device 510, for example. Local memory 508 is implemented as one or more non-persistent memory device(s) generally used during actual execution of the program code. Local memory 508 is an example of a runtime memory. Examples of local memory 508 include any of the various types of RAM suitable for use by a processor for executing program code. Bulk storage device 510 is implemented as a persistent data storage device. Examples of bulk storage device 510 include a hard disk drive (HDD), a solid-state drive (SSD), flash memory, a read-only memory (ROM), an erasable programmable read-only memory (EPROM), electrically erasable programmable read-only memory (EEPROM), or other suitable memory. Device 500 can also include one or more cache memories (not shown) that provide temporary storage of at least some program code in order to reduce the number of times program code must be retrieved from a bulk storage device during execution.

Examples of interface circuitry 506 include, but are not limited to, an input/output (I/O) subsystem, an I/O interface, a bus system, and a memory interface. For example, interface circuitry 506 can be implemented as any of a variety of bus structures and/or combinations of bus structures including a memory bus or memory controller, a peripheral bus, an accelerated graphics port, and a processor or local bus.

In one or more example implementations, processor(s) 502, memory 504, and/or interface circuitry 506 are implemented as separate components. Processor(s) 502, memory 504, and/or interface circuitry 506 may be integrated in one or more integrated circuits. The various components in device 500, for example, can be coupled by one or more communication buses or signal lines (e.g., interconnects and/or wires). Memory 504 may be coupled to interface circuitry 506 via a memory interface, such as a memory controller or other memory interface (not shown).

Device 500 can include one or more displays. Illustratively, for example, device 500 includes display 512 (e.g., a screen). Display 512 can be implemented as a touchscreen display capable of receiving touch input from a user. A touchscreen is a touch-sensitive display and/or a touch-sensitive pad that is capable of detecting contact, movement, gestures, and breaks in contact using any of a variety of available touch sensitivity technologies. Example touch-sensitive technologies include, but are not limited to, capacitive, resistive, infrared, and surface acoustic wave technologies, and other proximity sensor arrays or other elements for determining one or more points of contact with a touch-sensitive display and/or device. In other embodiments of device 500, such as a hearable (e.g., earbuds) that lacks a display, the user interface be an audio interface.

Device 500 can include an audio subsystem 514. Audio subsystem 514 can be coupled to interface circuitry 506 directly or through a suitable input/output (I/O) controller. Audio subsystem 514 can be coupled to a speaker 516 and a microphone 518 to facilitate voice-enabled functions, such as voice recognition, voice replication, digital recording, and telephony functions.

Device 500 can include one or more wireless communication subsystems 524. Each of wireless communication subsystem(s) 524 can be coupled to interface circuitry 506 directly or through a suitable I/O controller (not shown). Each of wireless communication subsystem(s) 524 is capable of facilitating communication functions. Examples of wireless communication subsystems 524 can include, but are not limited to, radio frequency receivers and transmitters, and optical (e.g., infrared) receivers and transmitters. The specific design and implementation of wireless communication subsystem 524 can depend on the particular type of device 500 implemented and/or the communication network(s) over which device 500 is intended to operate.

As an illustrative and non-limiting example, wireless communication subsystem(s) 524 may be designed to operate over one or more mobile networks, WiFi networks, short range wireless networks (e.g., a Bluetooth, UWB), and/or any combination of the foregoing. Wireless communication subsystem(s) 524 can implement hosting protocols such that device 500 can be configured as a base station for other wireless devices.

Device 500 may include IMU 520 and one or more sensors 522, each of which can be coupled to interface circuitry 506 directly or through a suitable I/O controller (not shown). Examples of sensor(s) 522 that can be included in device 500 include, but are not limited to, a motion sensor, a light sensor, and a proximity sensor to facilitate orientation, lighting, and proximity functions, respectively, of device 500. Other examples of sensors 522 can include, but are not limited to, a location sensor (e.g., a GPS receiver and/or processor) capable of providing geo-positioning sensor data, an electronic magnetometer (e.g., an integrated circuit chip) capable of providing sensor data that can be used to determine the direction of magnetic North for purposes of directional navigation, an accelerometer capable of providing data indicating change of speed and direction of movement of device 500 in 3D, and an altimeter (e.g., an integrated circuit) capable of providing data indicating altitude.

Device 500 further may include one or more input/output (I/O) devices 530 coupled to interface circuitry 506. I/O device(s) 530 can be coupled to interface circuitry 506 either directly or through intervening I/O controllers (not shown). Examples of I/O devices 530 include, but are not limited to, a track pad, a keyboard, a display device, a pointing device, one or more communication ports (e.g., Universal Serial Bus (USB) ports), a network adapter, and buttons or other physical controls. A network adapter refers to circuitry that enables device 500 to become coupled to other systems, computer systems, remote printers, and/or remote storage devices through intervening private or public networks. Modems, cable modems, Ethernet interfaces, and wireless transceivers not part of wireless communication subsystem(s) 524 are examples of different types of network adapters that may be used with device 500. One or more of I/O devices 530 may be adapted to control functions of one or more or all of sensors 522 and/or one or more of wireless communication subsystem(s) 524.

Memory 504 stores program code. Examples of program code include, but are not limited to, routines, programs, objects, components, logic, and other data structures. For purposes of illustration, memory 504 stores an operating system 532 and application(s) 534. In addition, memory 504 can store hearing management system program code 536, as described within this disclosure.

In an aspect, operating system 532 implemented in executable program code is executed by device 500 and, more particularly, by processor(s) 502, as are applications 534 and hearing management system program code 536. As such, operating system 532, application(s) 534 and hearing management system program code 536 may be considered an integrated part of device 500. Further, it should be appreciated that any data and/or program code used, generated, and/or operated upon by device 500 (e.g., processor(s) 502) are functional data structures that impart functionality when employed as part of device 500.

Device 500 is provided for purposes of illustration and not limitation. A device and/or system configured to perform the operations described herein can have a different architecture than illustrated in FIG. 5. The architecture can be a simplified version of the architecture described in connection with FIG. 5 that includes a memory capable of storing instructions and a processor capable of executing instructions. In this regard, device 500 may include fewer components than shown or additional components not illustrated in FIG. 5 depending upon the particular type of device that is implemented. In addition, the particular operating system and/or application(s) included can vary according to device type as can the types of I/O devices included. Further, one or more of the illustrative components can be incorporated into, or otherwise form a portion of, another component. For example, a processor may include at least some memory.

Device 500 can be implemented as a data processing system, a communication device, or other suitable system that is suitable for storing and/or executing program code.

Example implementations of devices that include some or all the elements of device 500 can include, but are not to limited to, a smart phone or other mobile device, a smartwatch or other wearable, and earbuds or other hearable.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise.

The term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without human intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The different types of memory, as described herein, are examples of a computer readable storage media. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, or the like.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the term "processor" means at least one hardware circuit. The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, "real-time" means a level of processing responsiveness that a user or system senses as sufficiently immediate for a particular process or determination to be made, or that enables the processor to keep up with some external process.

As defined herein, the term "responsive to" and similar language as described above, e.g., "if," "when," or "upon," mean responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

The term "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

The terms "user" and "individual" refer to a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowcharts or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method comprising:
   generating an audiogram based on responses of a user to signals conveyed to the user by a portable device;
   capturing sounds with the portable device;
   generating frequency-enhanced sounds by amplifying select frequencies of at least some of the captured sounds in real time based on the audiogram, and wherein the frequency-enhanced sounds are conveyed to the user;
   converting speech of the user during a conversation to text by execution of a voice recognition engine;
   detecting one or more predetermined words or repetition of a phrase within the speech of the user indicating the user does not understand the conversation; and
   in response to the detecting the one or more predetermined words or the repetition of the phrase, generating text captions of the conversation that visually supplement the enhanced sound and displaying the text captions on a display of the portable device.

2. The method of claim 1, comprising:
   generating a hearing assessment by analyzing the audiogram with the portable device; and
   providing with the portable device a hearing treatment recommendation in response to determining from the hearing assessment a potential hearing degradation of the user.

3. The method of claim 1, comprising:
   establishing with the portable device a wireless connection with a communication network for conveying the audiogram to a predetermined communication network site or importing from the predetermined communication network site an audiogram generated under direction of a hearing professional.

4. The method of claim 1, wherein
   the voice recognition engine uses a machine learning model to detect the one or more predetermined words or the repetition of the phrase based on classifying one or more words or phrases detected during the conversation.

5. The method of claim 1, comprising:
   detecting with the portable device potentially harmful sound during a monitoring phase; and
   responsive to determining that the potentially harmful sound exceeds a predetermined threshold, generating a warning conveyed to the user by the portable device.

6. The method of claim 1, comprising:
   providing a tinnitus therapy to the user comprising removing one or more identified tinnitus frequencies of the user from the captured sounds.

7. The method of claim 6, wherein
   the one or more identified tinnitus frequencies are identified by performing tinnitus sound matching using sounds generated by and conveyed to the user with the portable device.

8. The method of claim 1, comprising:
   in response to detecting a rest state of the user based on a motion sensor of the device, initiating an audible tinnitus treatment performed by the portable device, wherein the audible tinnitus treatment includes generating white noise while the user is in the rest state; and
   stopping generation of the white noise in response to detecting movement of the user by the motion sensor.

9. A system comprising:
   one or more processors configured to initiate operations including:
   generating an audiogram based on responses of a user to signals conveyed to the user by a portable device;
   capturing sounds with the portable device;
   generating frequency-enhanced sounds by amplifying select frequencies of at least some of the captured sounds in real time based on the audiogram, and wherein the frequency-enhanced sounds are conveyed to the user; converting speech of the user during a conversation to text by execution of a voice recognition engine;
   detecting one or more predetermined words or repetition of a phrase within the speech of the user indicating the user does not understand the conversation; and
   in response to the detecting the one or more predetermined words or the repetition of the phrase, generating text captions of the conversation that visually supplement the enhanced sound and displaying the text captions on a display of the portable device.

10. The system of claim 9, wherein the processor is configured to initiate operations including:
    generating a hearing assessment by analyzing the audiogram with the portable device; and
    providing with the portable device a hearing treatment recommendation in response to determining from the hearing assessment a potential hearing degradation of the user.

11. The system of claim 9, wherein the processor is configured to initiate operations including:
    establishing with the portable device a wireless connection with a communication network for conveying the audiogram to a predetermined communication network site or importing from the predetermined communication network site an audiogram generated under direction of a hearing professional.

12. The system of claim 9, wherein
    the voice recognition engine uses a machine learning model to detect the one or more predetermined words or the repetition of the phrase based on classifying one or more words or phrases detected during the conversation.

13. The system of claim 9, wherein the processor is configured to initiate operations including:
    detecting with the portable device potentially harmful sounds during a monitoring phase; and
    responsive to determining that the potentially harmful sounds exceed a predetermined threshold, generating a warning conveyed to the user by the portable device.

14. The system of claim 9, wherein the processor is configured to initiate operations including:

providing a tinnitus therapy to the user comprising removing one or more identified tinnitus frequencies of the user from the captured sounds.

15. The system of claim 14, wherein the one or more identified tinnitus frequencies are identified by performing tinnitus sound matching using sounds generated by and conveyed to the user with the portable device.

16. The system of claim 9, wherein the processor is configured to initiate operations including:
in response to detecting a rest state of the user based on a motion sensor of the device, initiating an audible tinnitus treatment performed by the portable device, wherein the audible tinnitus treatment includes generating white noise while the user is in the rest state; and
stopping generation of the white noise in response to detecting movement of the user by the motion sensor.

17. A computer program product, comprising:
a computer readable storage medium, and program instructions collectively stored on the computer readable storage medium, wherein the program instructions are executable by computer hardware of a portable device to initiate operations including:
generating an audiogram based on responses of a user to signals conveyed to the user by the portable device;
capturing sounds with the portable device;
generating frequency-enhanced sounds by amplifying select frequencies of at least some of the captured sounds in real time based on the audiogram, and wherein the frequency-enhanced sounds are conveyed to the user;
in response to detecting a rest state of the user based on a motion sensor of the portable device, initiating an audible tinnitus treatment performed by the portable device, wherein the audible tinnitus treatment includes generating white noise while the user is in the rest state; and
stopping generation of the white noise in response to detecting movement of the user by the motion sensor.

18. The computer program product of claim 17, wherein the program code is executable by the computer hardware to initiate operations including:
generating a hearing assessment by analyzing the audiogram with the portable device; and
providing with the portable device a hearing treatment recommendation in response to determining from the hearing assessment a potential hearing degradation of the user.

* * * * *